United States Patent
Zukowski

(10) Patent No.: US 9,579,187 B1
(45) Date of Patent: Feb. 28, 2017

(54) RADIALLY COMPLIANT PRESSURE INDICATING STENT GRAFT

(71) Applicant: Stanislaw L Zukowski, Flagstaff, AZ (US)

(72) Inventor: Stanislaw L Zukowski, Flagstaff, AZ (US)

( * ) Notice: Subject to any disclaimer, the term of this patent is extended or adjusted under 35 U.S.C. 154(b) by 0 days.

(21) Appl. No.: 15/040,132

(22) Filed: Feb. 10, 2016

(51) Int. Cl.
*A61F 2/07* (2013.01)
*A61F 2/90* (2013.01)

(52) U.S. Cl.
CPC .................. *A61F 2/07* (2013.01); *A61F 2/90* (2013.01); *A61F 2002/075* (2013.01); *A61F 2210/0014* (2013.01); *A61F 2240/002* (2013.01)

(58) Field of Classification Search
CPC ................ A61F 2/07; A61F 2/85; A61F 2/82
USPC .............................................. 623/1.13–1.48
See application file for complete search history.

(56) References Cited

U.S. PATENT DOCUMENTS

| | | |
|---|---|---|
| 5,591,230 A | 1/1997 | Horn et al. |
| 6,371,982 B2 | 4/2002 | Berg et al. |
| 6,572,649 B2 | 6/2003 | Berry et al. |
| 6,926,734 B1 | 8/2005 | Klein |
| 7,291,166 B2 | 11/2007 | Cheng et al. |
| 8,734,501 B2 | 5/2014 | Hartley et al. |
| 8,906,082 B2 | 12/2014 | Zilla et al. |
| 2001/0011188 A1 | 8/2001 | Berry et al. |
| 2005/0171598 A1* | 8/2005 | Schaeffer .................. A61F 2/07 623/1.35 |
| 2006/0155367 A1 | 7/2006 | Hines |
| 2008/0004687 A1 | 1/2008 | Barbut et al. |
| 2011/0218609 A1* | 9/2011 | Chobotov ................. A61F 2/06 623/1.11 |
| 2013/0060327 A1* | 3/2013 | Shokoohi ................ A61F 2/856 623/1.42 |
| 2013/0144374 A1* | 6/2013 | Zilla ......................... A61F 2/06 623/1.15 |
| 2014/0324154 A1* | 10/2014 | Shalev ...................... A61F 2/07 623/1.13 |
| 2016/0143754 A1* | 5/2016 | Orion ....................... A61F 2/82 623/1.15 |

\* cited by examiner

*Primary Examiner* — Suzette J Gherbi

(57) ABSTRACT

A radially compliant pressure indicating stent graft is radially compliant from a free stent graft diameter to an expanded stent graft diameter. A radially compliant slant is attached to a graft having stored circumferential length between attachment points. A slant may be expanded and affixed to the graft or the graft may be constricted radially and the stent attached to the constricted graft. The radially compliant stent graft may expand radially to a free graft diameter and the graft may be non-elastic and/or no compliant. As the stent graft approaches the free graft diameter, the force to expand further may increase rapidly.

14 Claims, 16 Drawing Sheets

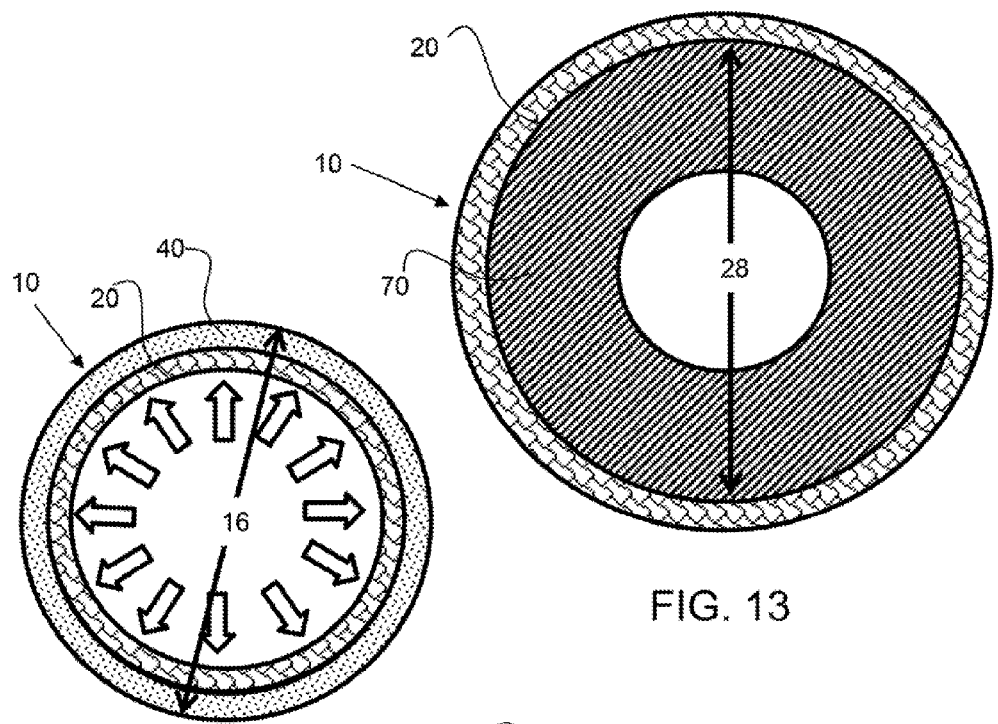
FIG. 13
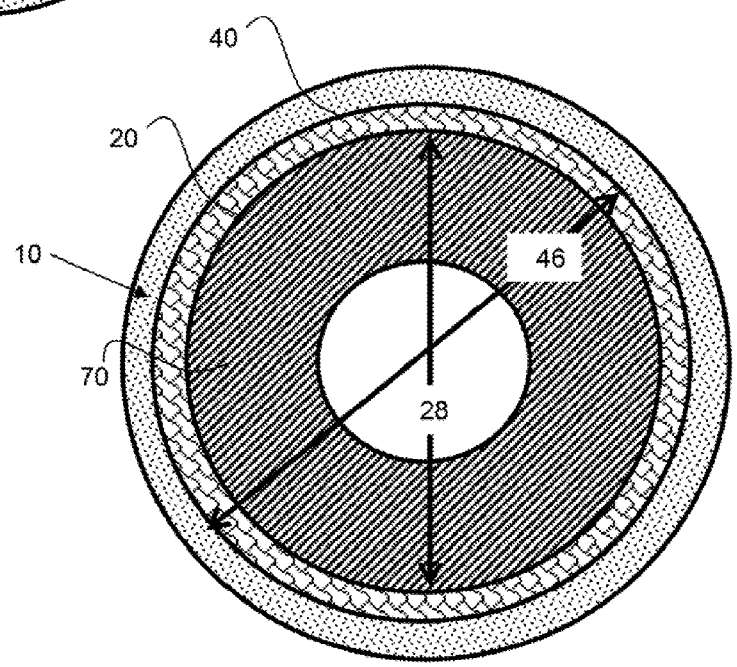
FIG. 15
FIG. 14

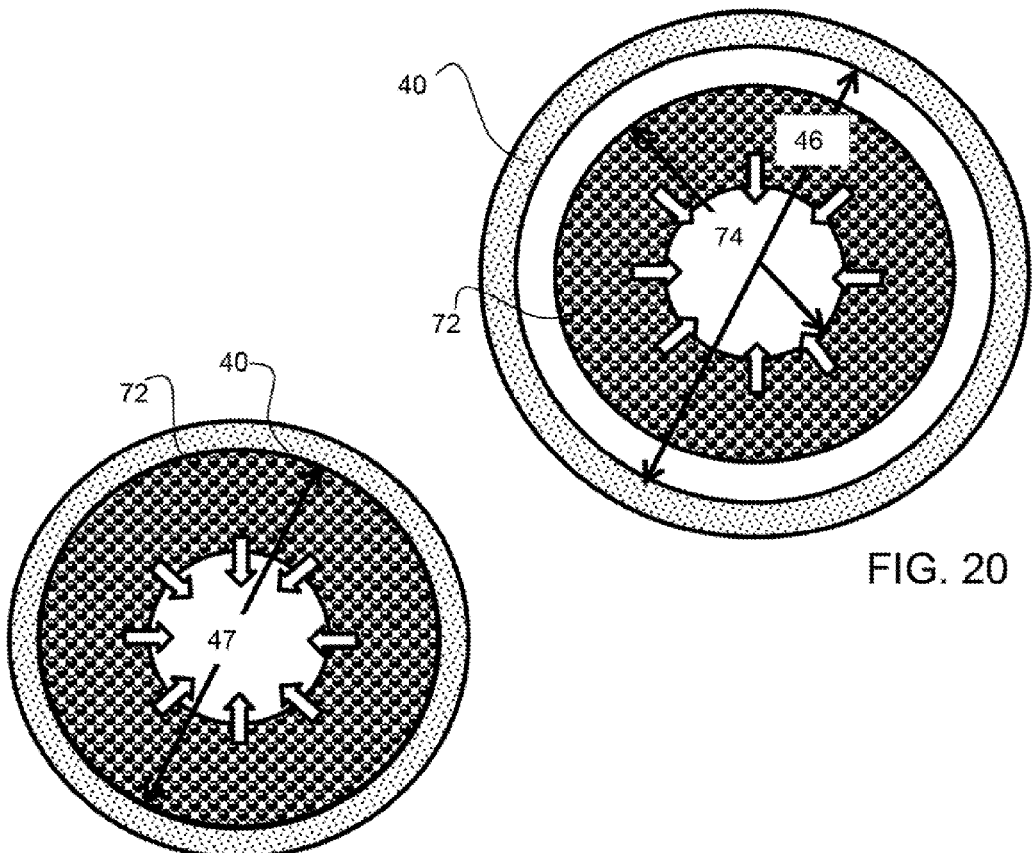
FIG. 20
FIG. 21
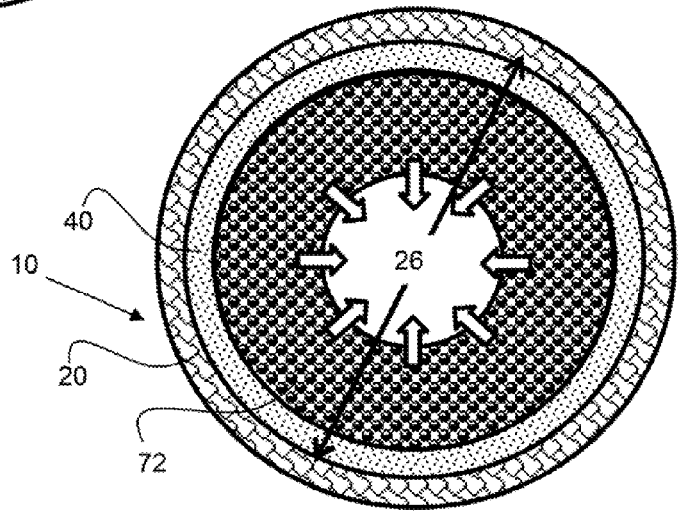
FIG. 22

RADIALLY COMPLIANT PRESSURE INDICATING STENT GRAFT

BACKGROUND OF THE INVENTION

Field of the Invention

The present invention relates to radially compliant stent grafts that may be used to indicate a pressure differential across the wall of the radially compliant stent graft.

Background

Stents made out of super elastic materials, such as Nitinol, have been used to produce radially compliant stents. However, grafts made out of fluoropolymers, such as expanded PTFE, are not elastic. Stents and grafts are combined to produce self-expanding stent grafts that are radially compliant in compression only, as the graft is not elastic. The graft can be radially compressed but cannot be radially expanded as it will stretch and damage the graft material. Typically, a stent graft is constricted down in diameter and retained in this constricted state until positioned within the vasculature for deployment, where the stent graft is expanded radially within the vasculature. In most cases, the stent graft is oversized, wherein the stent graft diameter in a free state is larger than the diameter of the vasculature, thereby ensuring that the stent graft is retained in position. The stent graft is radially compliant only in compression and will expand radially only to the diameter of the non-elastic graft. In addition, the inability of conventional stent graft to radially comply with pulse pressure profiles can have deleterious cardiovascular effects, wherein the load of the heart is increased. In addition, a systolic pulse from the heart is not attenuated by non-compliant conventional stent grafts. There exists a need for a stent graft that is radially compliant in both expansion and compression, more like healthy native vascular tissue.

SUMMARY OF THE INVENTION

The invention is directed to a radially compliant pressure indicating stent graft that is radially compliant in both radial expansion and radial compression, or reduction in diameter. The radially compliant pressure indicating stent graft of the present invention more closely mimics healthy native tissue and therefore may reduce trauma within the vasculature system. An exemplary radially compliant pressure indicating stent graft has an oversized graft retained by a radially compliant stent and may help to reduce high blood pressure. The oversized graft may be attached to a radially compliant stent by attachments to produce a stored circumferential length of graft material between the attachments. In one embodiment, a stent is expanded from a free stent diameter to an expanded stent diameter and attached to the graft while in this expanded state. When the stent constricts the stent graft from this expanded state down to substantially the free stent graft diameter the graft is constricted radially and forms stored circumferential lengths of material between the attachments to the stent. In another embodiment, a graft is constricted radially from a free graft diameter to a constricted graft diameter and attached to a stent while in this constricted state. For the purposes of brevity, the term "radially compliant pressure indicating", may be referred to herein as simply a radially compliant stent graft or a simply a stent graft.

A stent of the, present invention may be made out of a highly or super-elastic alloy that can be heat-set to have a first free diameter. In an exemplary embodiment, the stent comprises or consists of Nitinol. Other suitable materials for stent manufacture include, but are not limited to, Elgiloy, titanium, tantalum, stainless steel, alloys of, Ag-Cd, Au-Cd, Cu-Al-Ni, Cu-Ss, Cu-Zn, Cu-Zn-Si, Cu Zn-Sn, Cu-Zn-Al, In-Ti, Ni, Al, Ni-Ti, Fe-Pt, Mn-Cu, Fe-Mn-Si. A stent of the present invention is radially compliant having an inherent recovery force that will return the stent to a free stent diameter when external forces are removed. A stent may be cylindrical in shape having an outer and inner diameter. A stent may be made out of a super-elastic material such as Nitinol wire using a configuring mandrel and heat treatment to retain the shape, and may be made through any conventional means. A stent may be formed from super-elastic wire that is formed to create a stent. In another embodiment, a super-elastic material can be a Nitinol tube from which a stent is laser cut and heat expanded, to create a desired shape and size. An exemplary stent may be a contiguous stent wherein the stent elements are all connected into a single one piece article. In another exemplary embodiment, a stent may comprise discrete elements that are configured coaxially with the graft. In still another embodiment the stent comprise a helical undulating element, such as a super-elastic wire configured coaxially with and attached to the graft. An exemplary stent comprises extensions that are connected at nodes to form cells, or openings in the stent formed by the extensions.

An exemplary graft is substantially non-elastic and non-radially compliant by itself. An exemplary graft material is made from a fluoropolymer or any other suitable plastic material that is biocompatible such as Dacron, polyester, polytetrafluoroethylene (PTFE), and nylon. A graft may be porous, semi-permeable or totally impermeable to fluids such as blood. In a preferred embodiment, a graft is impermeable to blood and other liquids, thereby enabling the exclusion of blood flow to an aneurysm. An exemplary graft is made from expanded polytetrafluorethylene (ePTFE) and comprises nodes interconnected by fibrils. An ePTFE material may be a tube and may, be porous and permeable or completely impermeable. An exemplary graft is non-elastic and has a free graft diameter, or a diameter when no external forces are applied. When the graft is attached to the stent graft of the present invention it has a constricted graft diameter that is less than the free graft diameter and includes stored length between attachments. The stent graft of the present invention may expand and automatically return to a free stent graft diameter from an expanded graft diameter that is less than the free graft diameter.

The radially compliant stent graft of the present invention may be an endovascular stent graft having a generally tubular body, ie cylindrical, and be configured to assume a radially-compressed delivery state and a radially expanded deployed state. A radially compliant stent graft, as described herein, may be slightly oversized for the vessel it is intended to assure that the stent graft will remain fixed in position within the vessel after deployment. The radially compliant stent graft of the present invention is ideally suited for excluding flow to an aneurysmal sack, wherein the stent graft is configured across the aneurysmal sack with opposing ends retained in healthy vessel tissue. A radially compliant stent graft of the present invention may be configured across an aneurysmal sack and may reduce stress or trauma associated with pressure changes of the blood flowing therethrough. Repetitive changes in blood pressure from systolic to diastolic can cause a stiff and non-compliant stent graft to rub against the wall of the vessel. The radially compliant stent graft of the present invention will expand and contract with the changes in blood pressure and move with the vessel, thereby reducing friction. An exemplary stent graft of the present invention, having high physiological compliance, may minimize the effect of the stent graft on the pulse profile of blood within the vessel. An exemplary stent graft of the present invention will radially pulsate with the systolic cycle and mimic young healthy vasculature tissue. The radially compliant stent graft of the present invention will expand due to blood pressure changes in the aneurysmal sack, which may relieve or reduce stress and/or friction between the stent graft, and the healthy vessel on one or both sides of the aneurysmal sack. The expansion of the stent graft within the aneurysmal sack may prevent local pressure spike.

The stent graft of the present invention may be used to determine the pressure within a vessel and/or to determine if an aneurysm has been successfully excluded. An aneurysmal sack will have reduced pressure if the blood flow to the aneurysmal sack is excluded or prevent by the implantation of a stent graft. A radially compliant stent graft with a known diameter versus pressure profile, as described herein, can be used to determine the pressure difference within the interior of the stent graft and the aneurysmal sack, or across the wall of the stent graft. If the blood flow is excluded to the aneurysmal sack, the pressure within the sack should be reduced and the diameter of the stent, graft, as determine by fluoroscopy, or other imaging techniques, should be expanded above the free stent diameter, thereby reflecting the pressure gradient across the stent graft wall. The stent graft should expand and contract with the vessel according to the systolic and diastolic blood pressure. In the event the blood flow to the aneurysmal sack is not prevented, the sack may have the same, or similar pressure as the blood flow through the stent graft. In this case, the diameter of the stent graft will be substantially that of the free stent graft diameter since the pressure forces acting on the outer surfaces of the stent graft will be the same as those acting inside the stent graft.

In an exemplary embodiment, a graft is configured over a mandrel that is substantially the same diameter as the free graft diameter. A stent, having free stent diameter less than the free graft diameter is then radially expanded and configured over the graft, being configured with a free graft diameter on the mandrel. The stent may then be attached to the graft by an adhesive or bondable tape that is wrapped over the stent and bonds the stent to the graft. The stent graft may then be removed from the mandrel and the stent will cause the stent graft to constrict radially to a free stent graft diameter that, is less than the free graft diameter, thereby constricting the graft to a constricted graft diameter. The graft will have stored circumferential length of graft material that enables the stent graft to expand radially back to substantially the free graft diameter from the free stent graft diameter. The stent graft is radially compliant in both expansion and compression. In another exemplary embodiment, the stent is placed over a mandrel having a diameter that is substantially that of a free graft diameter, and the graft is placed over the stent and subsequently attached to the graft before the stent graft is removed off the mandrel to create a radially compliant stent graft. It is to be understood that a stent may be placed over a mandrel that larger than the free stent diameter and about the same or less than the free graft diameter, to impart both radial compliance in both expansion and constriction, as described in the previous method.

In still another embodiment, a vacuum mandrel is used to reduce the diameter of the graft from a free graft diameter to a constricted graft diameter before a stent is attached thereto. Again, the stent may be configured inside of or outside of the graft.

In another embodiment, a funnel or constriction tube is used to reduce the diameter of the graft. For example, a graft may be pulled through a funnel into a tube having a diameter less than the free graft diameter. A stent may be configured within or overtop of the graft before it is pulled through the funnel into the constriction tube. Adhesive may be applied or configured to bond the graft to the stent while in the constriction tube. In an exemplary embodiment, a stent is placed within a graft, as the graft has a free graft diameter that is greater than the free stent diameter. The stent and/or graft may be coated with an adhesive that is a thermoplastic. The stent and graft may be pulled into the constriction tube together and then heated to bond the graft to the stent and form attachments. The stent graft may then be removed from the constriction tube to produce a radially compliant stent graft. A stent may be attached to a graft to form attachments wherein there is stored length between the attachments. The attachments may be along the surface of the stent, wherein the stent and/or graft is configured with an adhesive before the two components are configured concentrically together. A stent may be stitched to a graft. A bondable tape may configured between the two components or on a first component before the second component is configured concentrically with the first component.

The summary of the invention is provided as a general introduction to some of the embodiments of he invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of his specification, illustrate embodiments of the invention, and together with the description serve to explain the principles of the invention.

DETAILED DESCRIPTION OF THE ILLUSTRATED EMBODIMENTS

Figure 1:
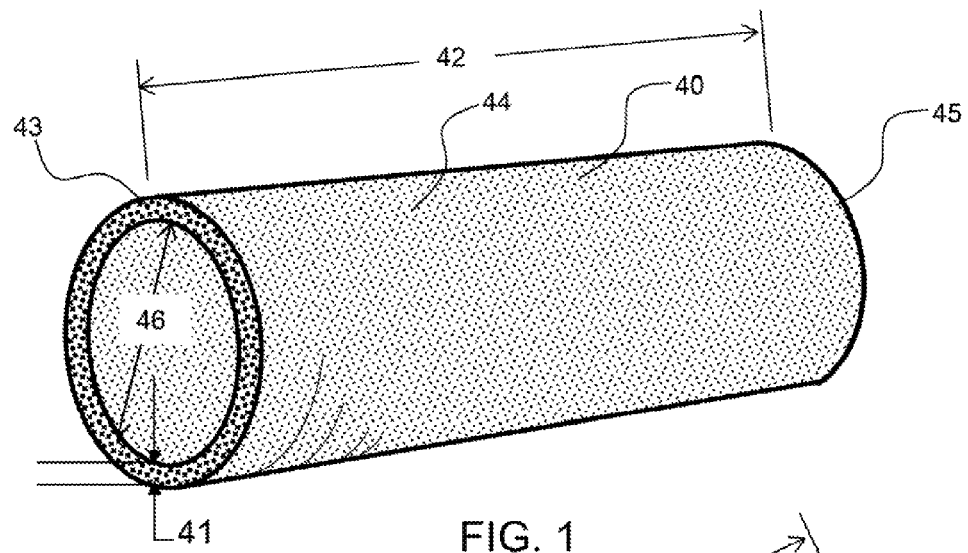

FIG. 1 shows a perspective view of an exemplary graft that is a cylindrical tube having a free graft diameter.

Figure 2:
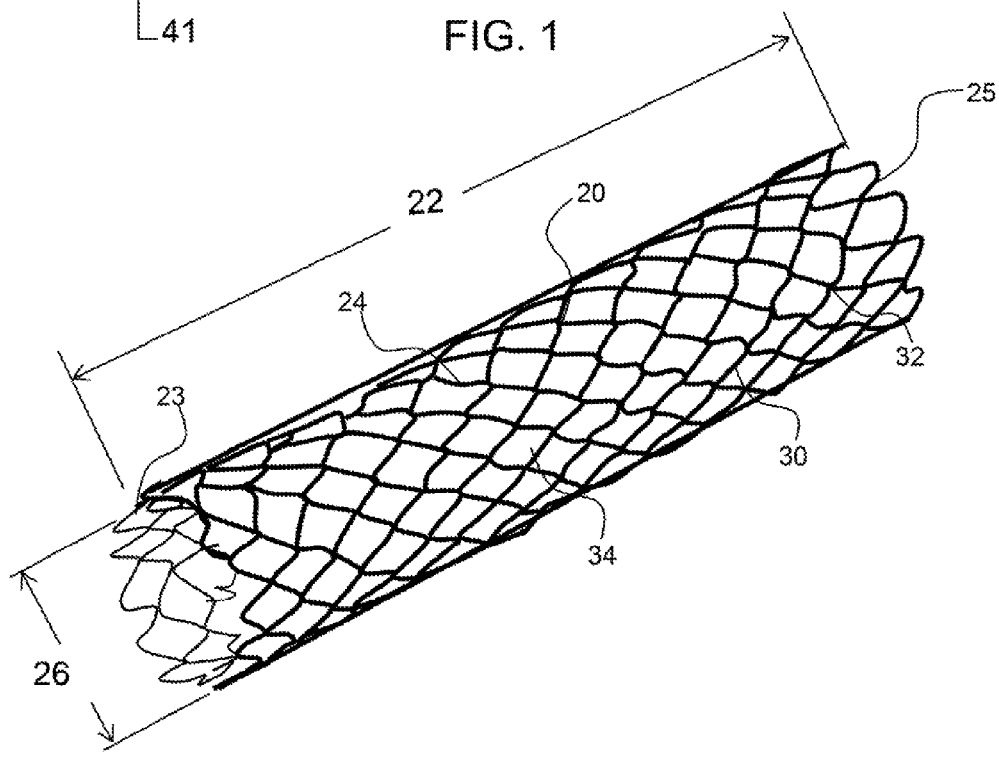

FIG. 2 shows a perspective view of an exemplary stent having a free stent diameter.

Figure 3:
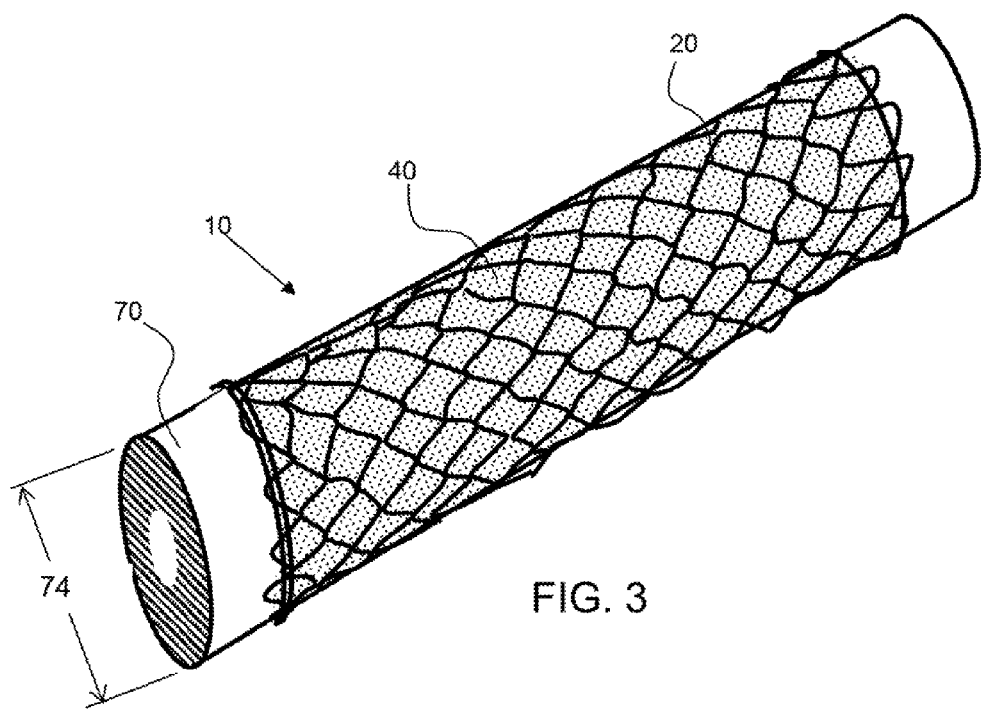

FIG. 3 shows a perspective view of an exemplary stent graft having the graft configured around a mandrel having a diameter that is substantially the same as the free graft diameter, and the stent configured around the outer surface of the graft, wherein the stent is radially expanded from a free stent diameter to the free graft diameter and configured over the graft.

Figure 4:
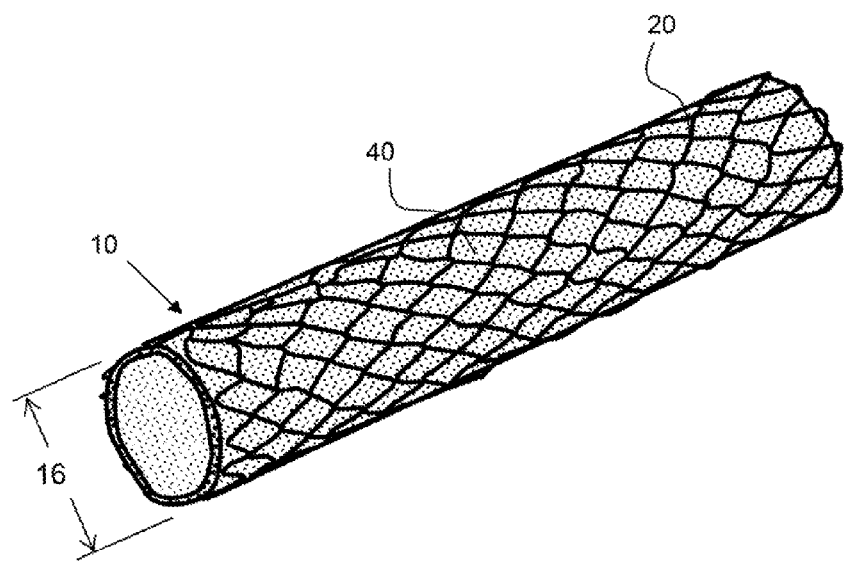

FIG. 4 shows a perspective view of the exemplary stent graft of FIG. 3 removed from the mandrel wherein the stent has radially compressed the stent graft down in diameter to less than the free graft diameter.

Figure 5:
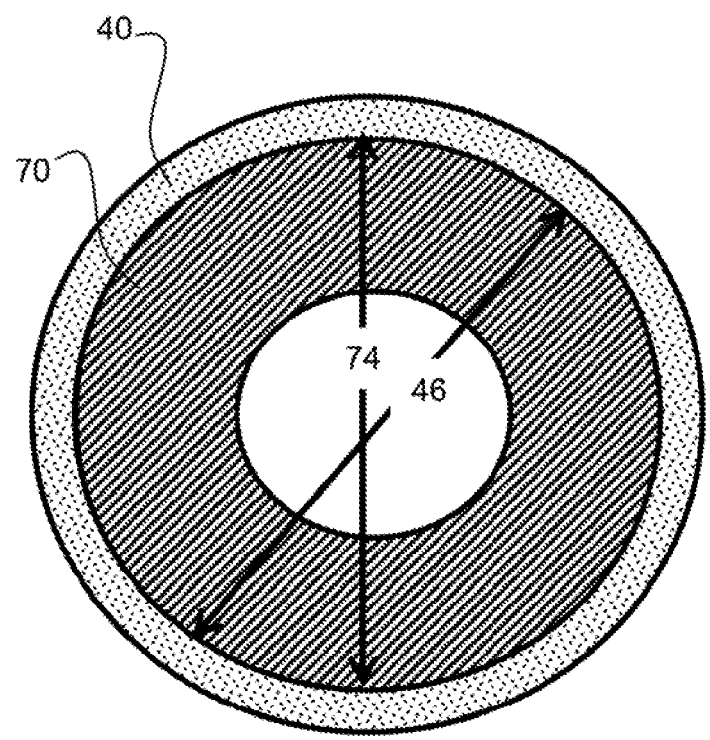

FIG. 5 shows a cross-sectional view of an exemplary graft configured over a mandrel having a diameter that is substantially the same as the free graft diameter.

Figure 6:
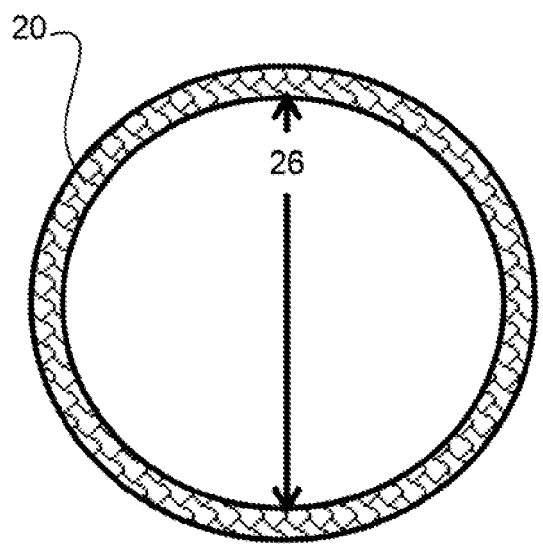

FIG. 6 shows a cross-sectional view of an exemplary stent having a free stent diameter that is less than the free graft diameter.

Figure 7:
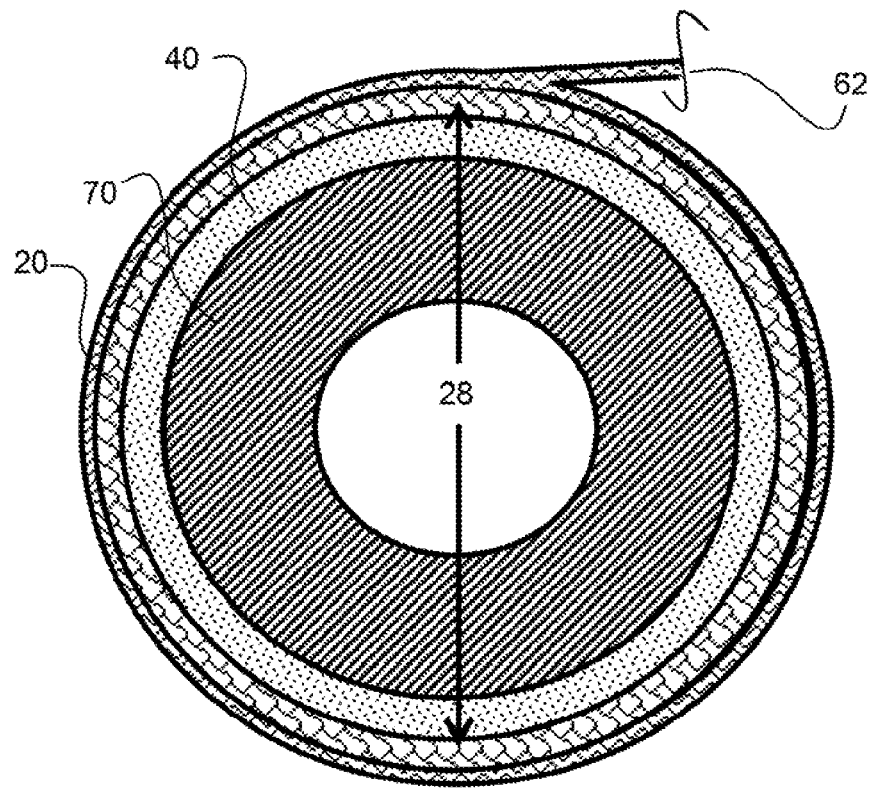

FIG. 7 show the exemplary graft shown in FIG. 5 with the stent shown in FIG. 6 expanded radially and configured over the graft and mandrel and a bondable tape wrapped around it.

Figure 8:
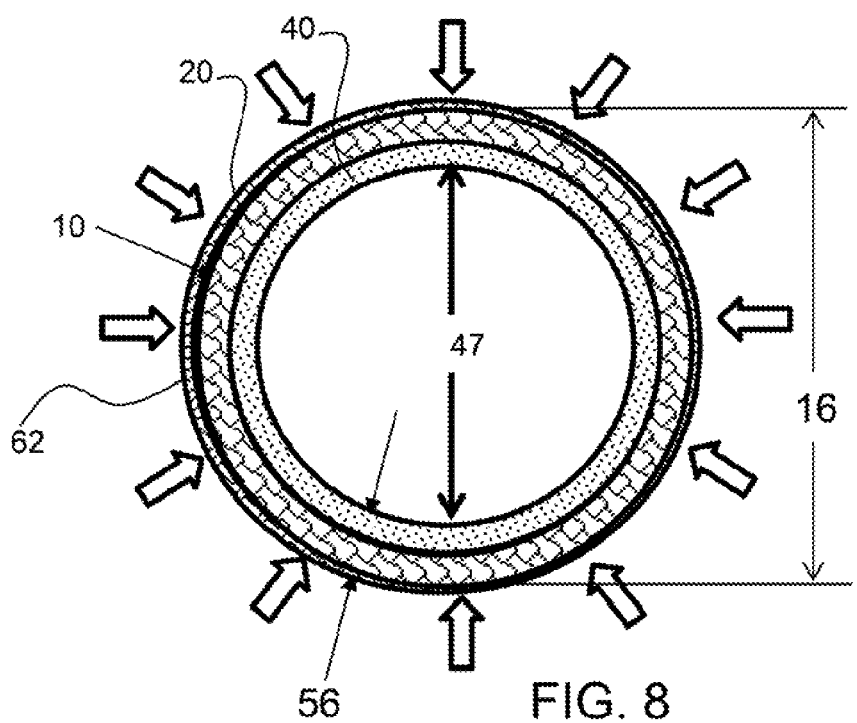

FIG. 8 shows the exemplary stent graft shown in FIG. 7 removed from the mandrel and radially compressed to a stent graft free diameter that is less than the graft free diameter.

Figure 9:
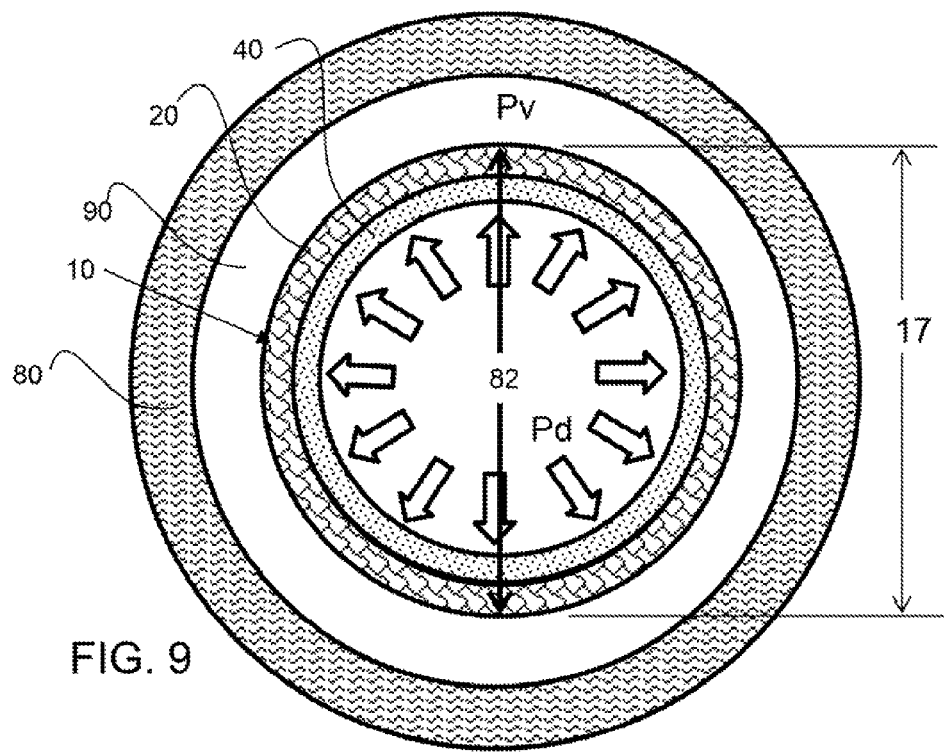

FIG. 9 shows a cross-sectional view of the stent graft shown in FIG. 8 radially expanded by a fluid pressure within the stent graft, as depicted by the arrows pointing radially outward.

Figure 10:
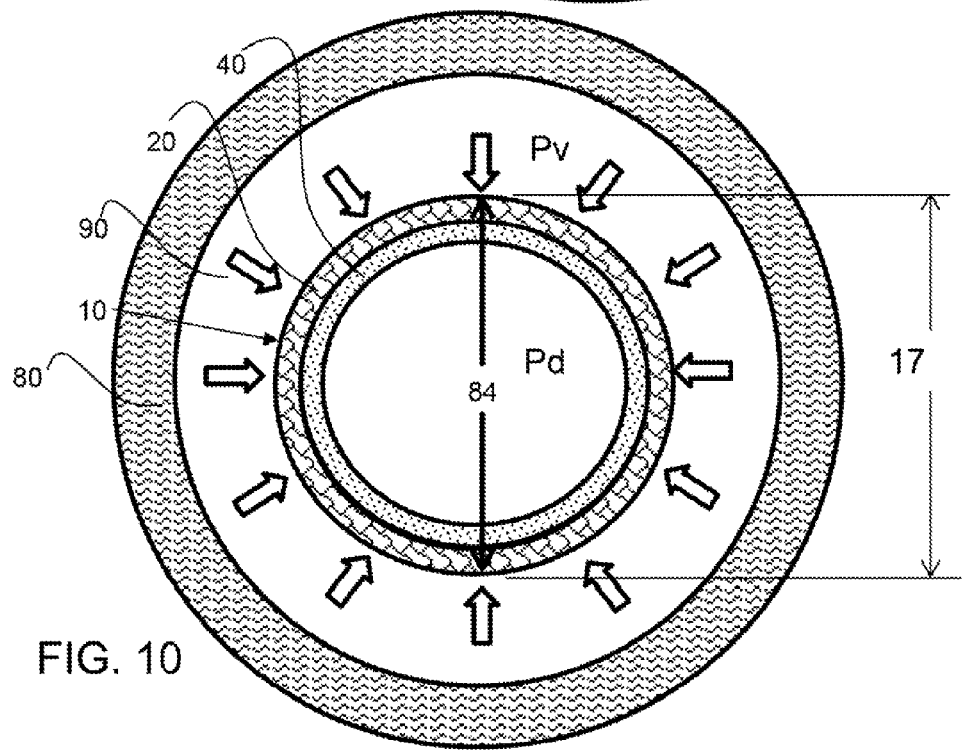

FIG. 10 shows a cross-sectional view of the stent graft shown in FIG. 9 radially compressed by a force exerted by the stent.

Figure 11A:
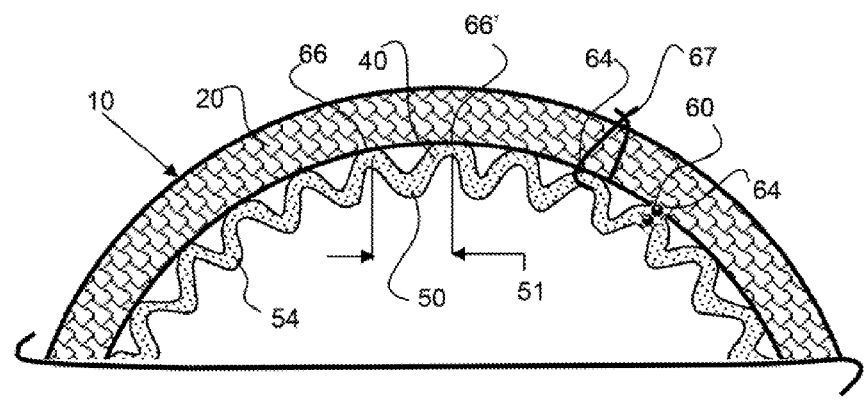

FIG. 11A shows a portion of a cross-section of an exemplary stent graft, having attachment points between the graft and stent and the graft having stored circumferential length between these attachment points.

Figure 11B:
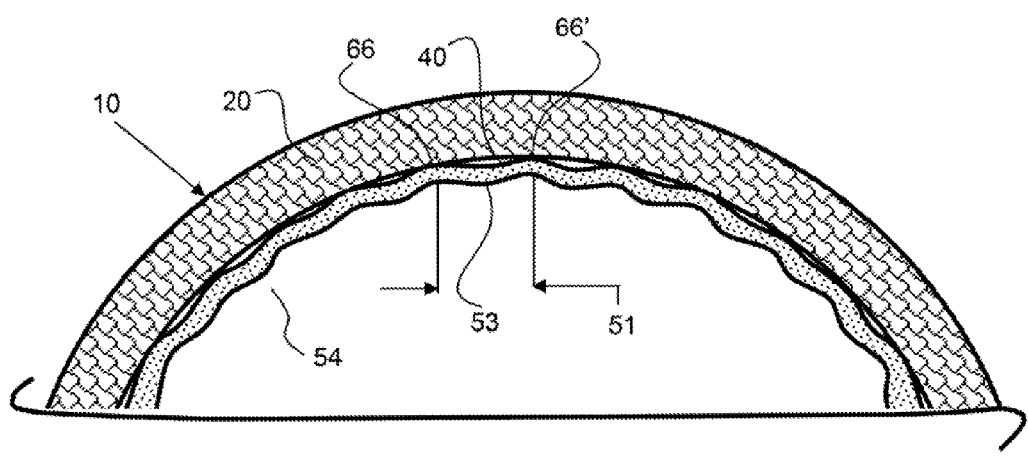

FIG. 11B shows the stent graft of FIG. 11A expanded in diameter, or radially.

Figure 12:
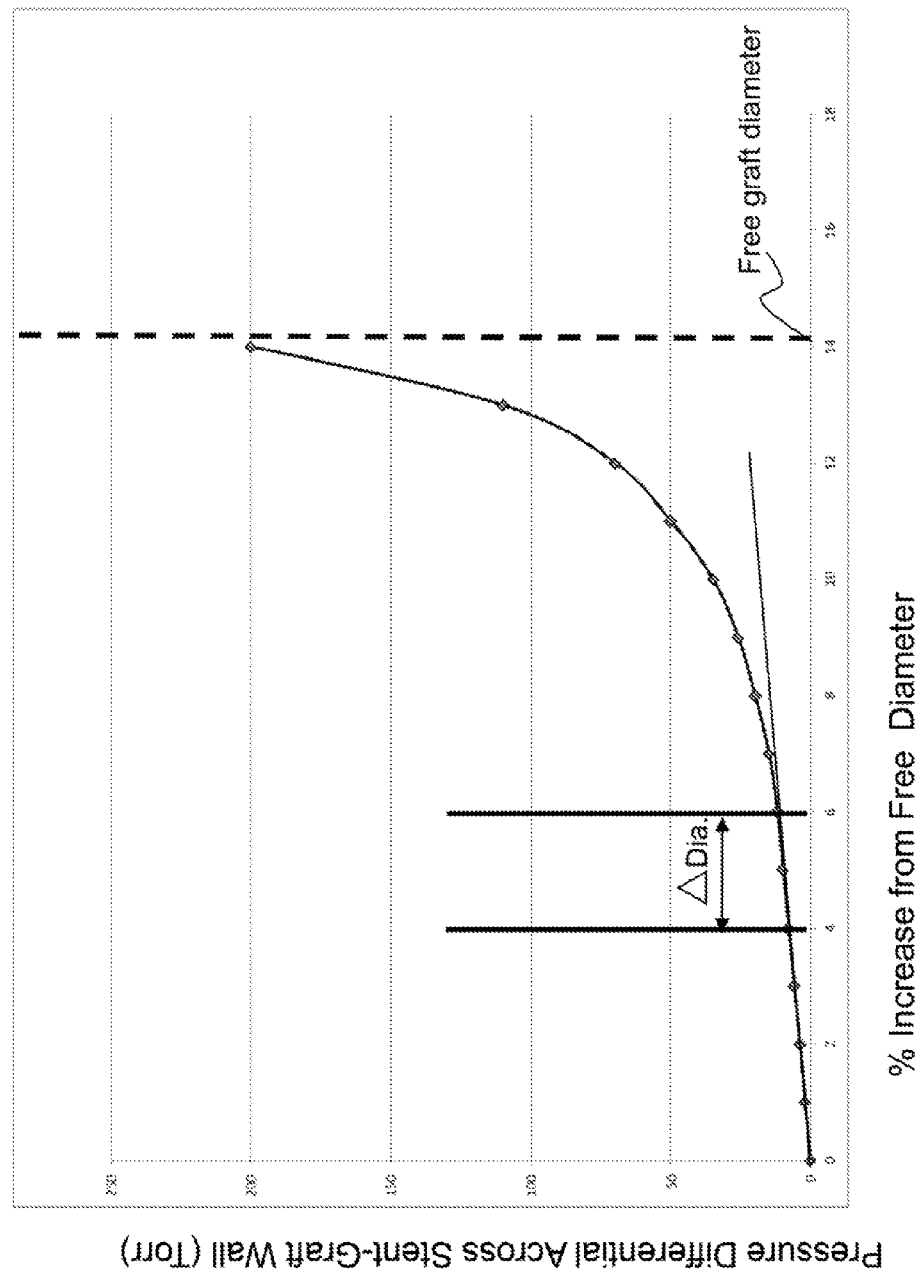

FIG. 12 shows a graphical representation of the pressure required to radially expand an exemplary stent graft, as described herein.

FIG. 13 shows a cross-sectional view of the stent shown in FIG. 6 configured over a mandrel that is larger in diameter than the stent free diameter.

FIG. 14 shows the mandrel and stent graft shown in FIG. 13 with a graft configured over the radially expanded stent.

FIG. 15 shows a cross-sectional view of the exemplary stent graft shown in FIG. 14 removed from the mandrel and radially compressed to a stent graft free diameter.

Figure 16:
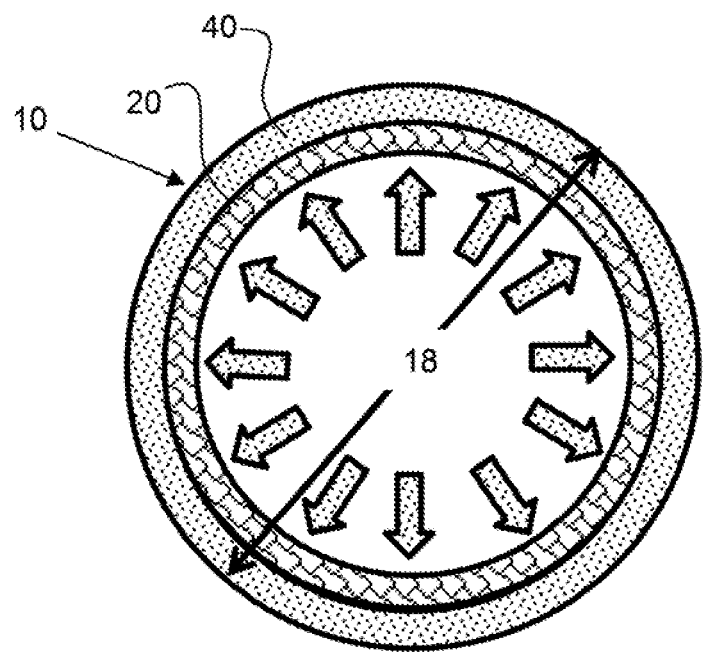

FIG. 16 shows a cross-sectional view of the exemplary stent graft shown in FIG. 15 radially expanded by a pressure within the stent graft.

Figure 17:
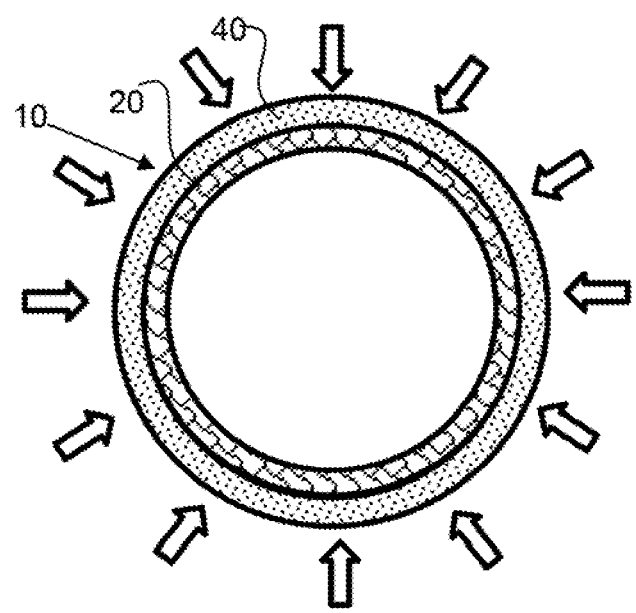

FIG. 17 shows a cross-sectional view of the exemplary stent graft shown in FIG. 16 resiliently returned to the stent graft free diameter by a radially compressive force exerted on the stent graft by the stent.

Figure 18:
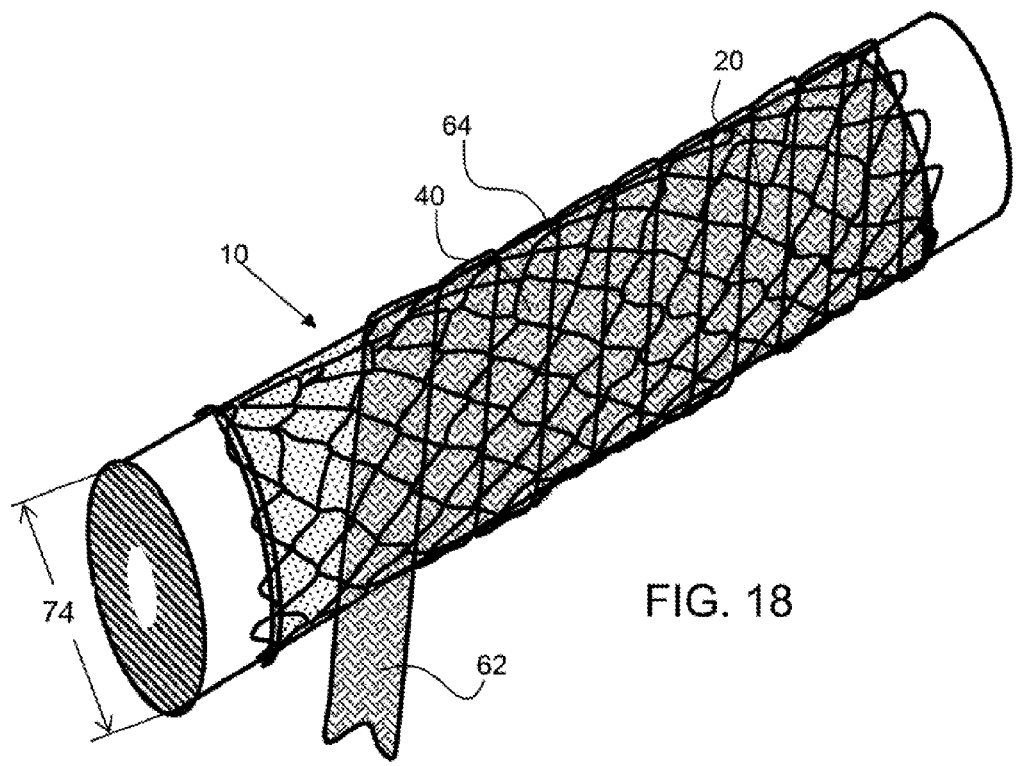

FIG. 18 shows a perspective view of an exemplary stent graft being wrapped with a bondable tape to bond the stent to the graft.

Figure 19:
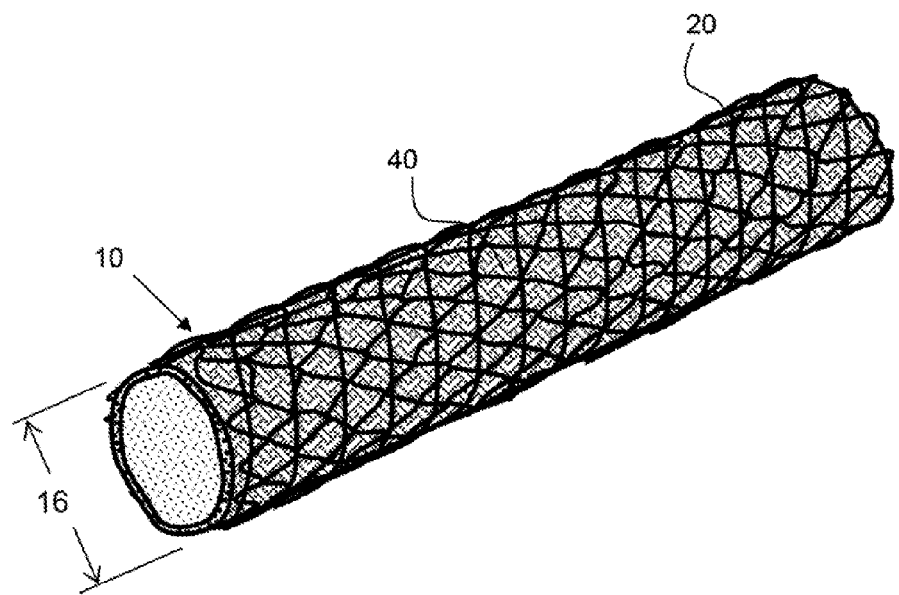

FIG. 19 shows a perspective view of the exemplary stent graft shown in FIG. 18 removed from the mandrel and having a free stent diameter that is less than the mandrel diameter.

FIG. 20 shows a cross-sectional view of an exemplary vacuum mandrel and a graft configured thereover.

FIG. 21 shows a cross-sectional view of the graft shown in FIG. 20 drawn down radially onto the vacuum mandrel.

FIG. 22 shows a cross-sectional view of the stent configured over the graft shown in FIG. 21.

Figure 23:
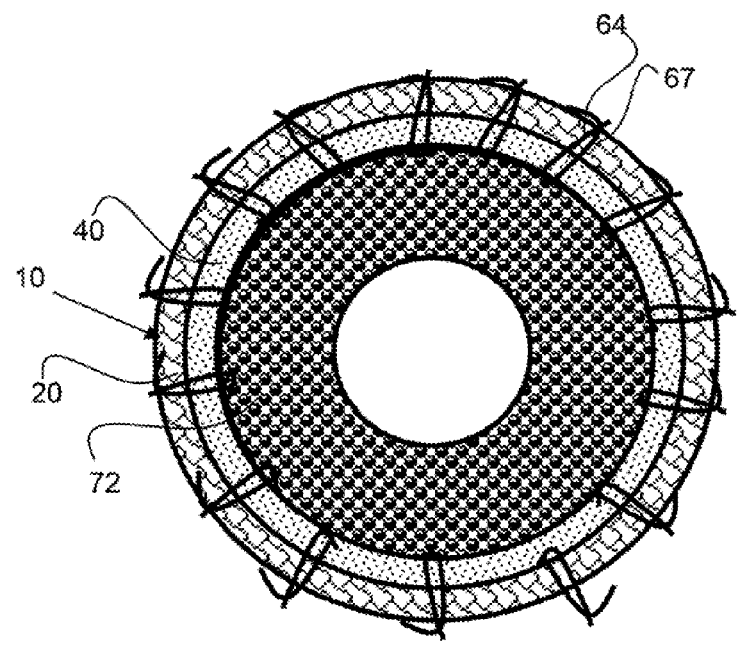

FIG. 23 shows cross-sectional view of the stent and graft configured on the vacuum mandrel, as shown in FIG. 22, with stitch attachments attaching the stent to the graft.

Figure 24:
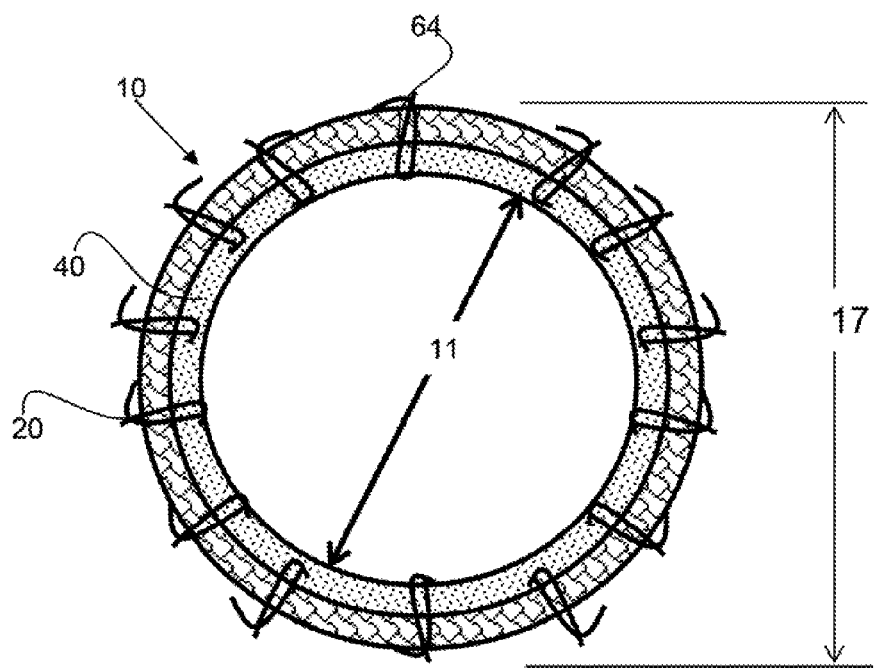

FIG. 24 shows the radially compliant stent graft removed from the mandrel of FIG. 23.

Figure 25:
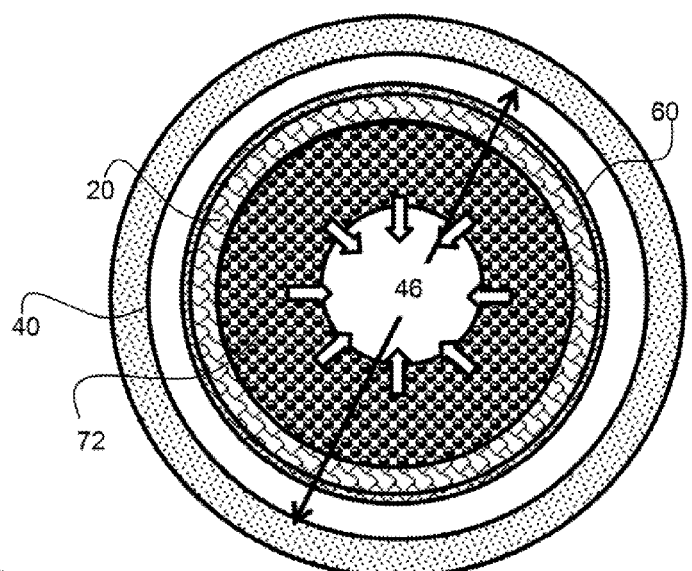

FIG. 25 shows a cross-sectional view of an exemplary vacuum mandrel having a stent and a graft configured thereover and an adhesive configured on the stent.

Figure 26:
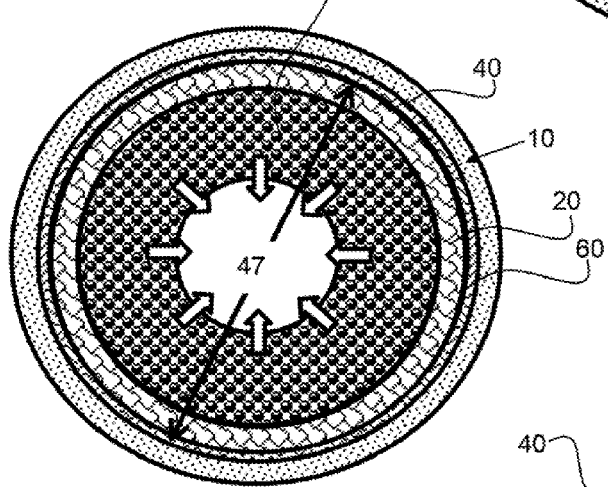

FIG. 26 shows a cross-sectional view of the graft shown in FIG. 25 drawn down radially onto the vacuum mandrel.

Figure 27:
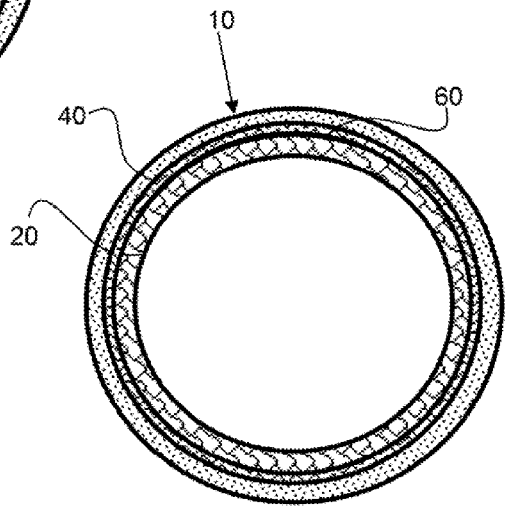

FIG. 27 shows a cross-sectional view of the radially compliant stent graft removed from the mandrel of FIG. 26 and having the adhesive forming attachments between the stent and the graft.

Figure 28:
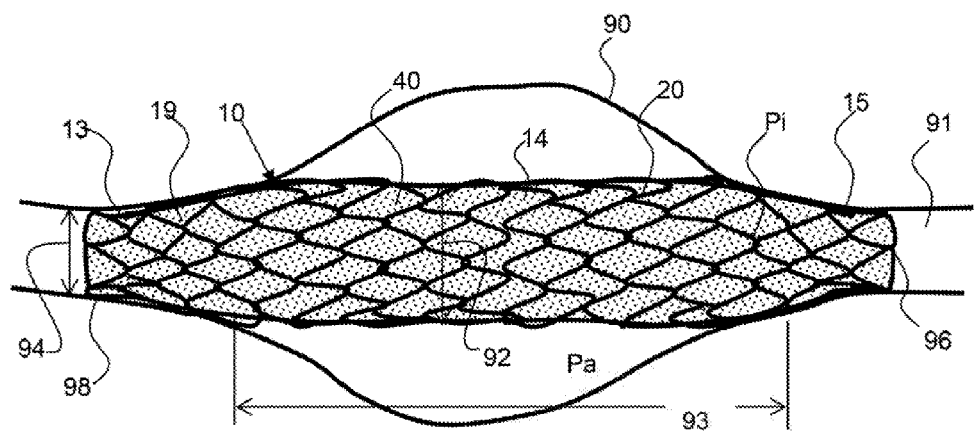
Figure 29:
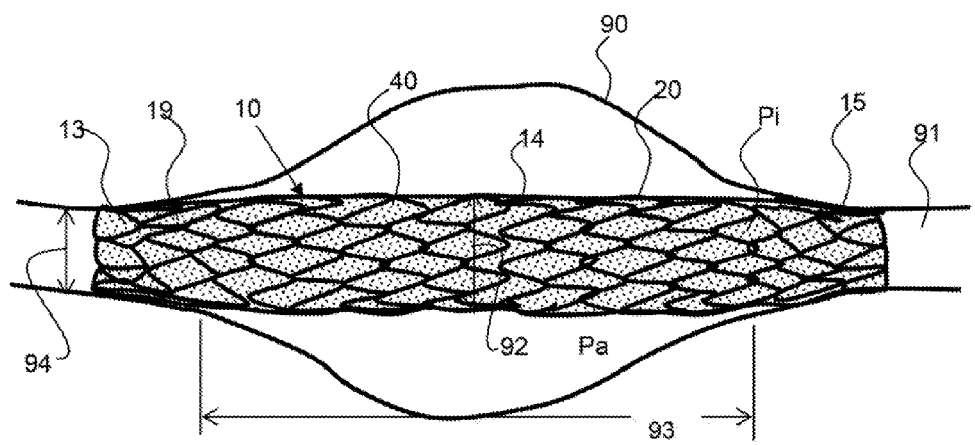

FIGS. 28 and 29 show an exemplary radially compliant stent graft disposed across an aneurysmal sack of an artery.

Figure 30:
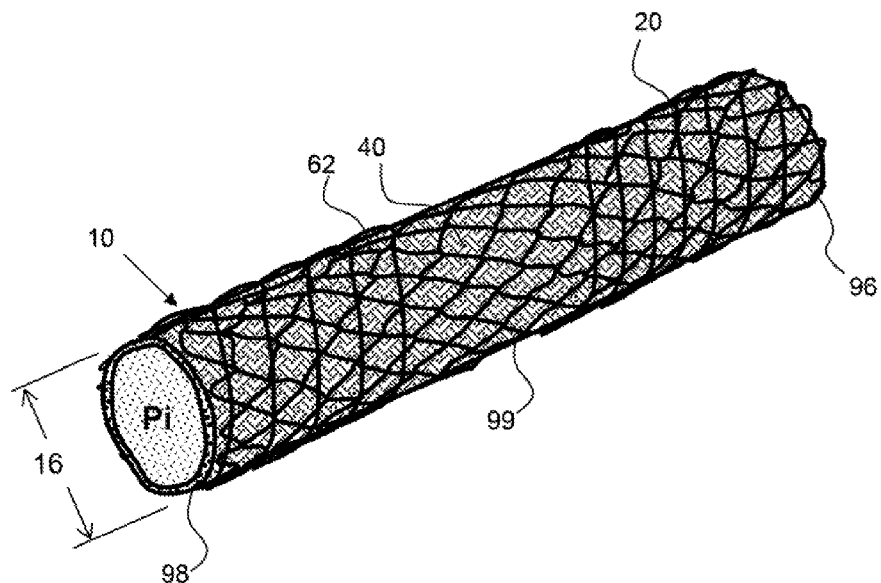

FIG. 30 shows a perspective view of an exemplary radially compliant stent graft having a pressure indicating section.

Figure 31:
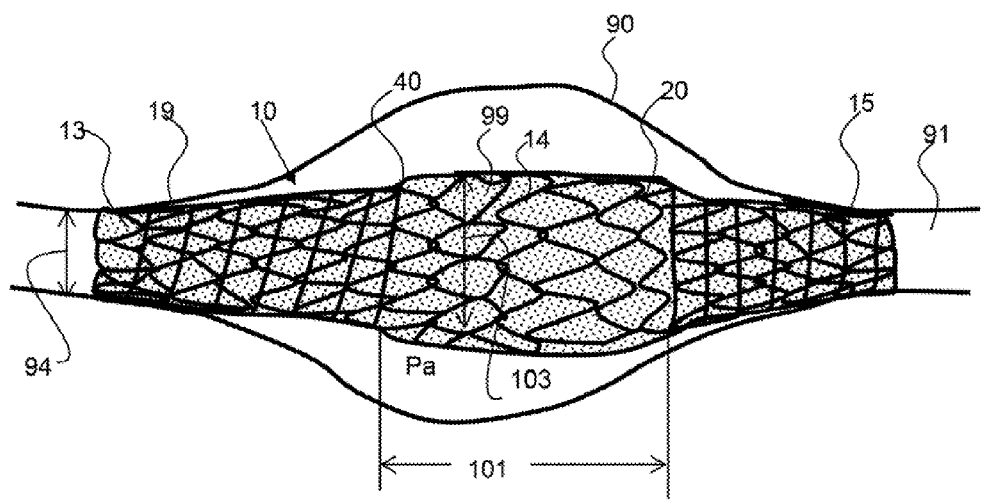

FIG. 31 shows the exemplary radially compliant stent graft of FIG. 30 disposed across an aneurysmal sack of an artery.

Figure 32:
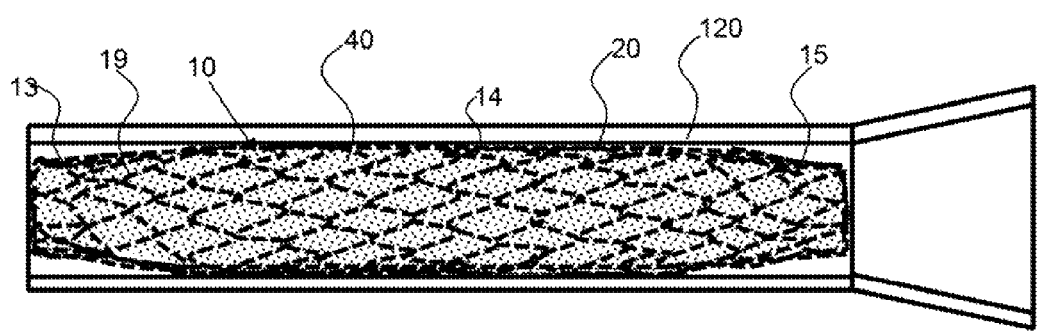

FIG. 32 shows an exemplary radially compliant stent graft configured in a constriction tube.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications improvements are within the scope of the present invention.

As shown in FIG. 1, an exemplary graft 40 has a length 42 from a proximal end 43 to a distal end 45 and a middle portion 44 therebetween. The graft has a wall thickness 41 and an aperture extending through the cylindrical tube. The graft has a free graft diameter 46 that is the diameter of the graft with no forces exerted to increase or decrease the diameter. in an exemplary embodiment, the graft is radially non-compliant having substantially no elastic properties.

As shown in FIG. 2, an exemplary stent 20 has a length 22 from a proximal end 23 to a distal end 25 and a middle portion 24 therebetween. The stent has a free diameter 26 that is the diameter of the stent with no external forces applied to change the diameter of the stent. The stent is radially compliant and will return automatically to the free diameter after expansion or contraction to a diameter of a different size. The exemplary stent comprises extensions 30 that are coupled together at nodes 32, or intersection of the extensions. The extensions form cells 34, or open areas within the stent defined by a perimeter of extensions.

As shown in FIG. 3, an exemplary stent graft 10 has the graft 40 configured around a mandrel 70 having a diameter 74 that is substantially the same as the free graft diameter 46, as shown in FIG. 1. An exemplary stent 20 is configured around the outer surface of the graft, wherein the stent is radially expanded from a free stent diameter to an expanded stent diameter that may be substantially the free graft diameter 46, as shown in FIG. 1. The stent is in radial tension, meaning it has inherent forces that act to reduce the diameter back to the free stent diameter.

As shown in FIG. 4, the exemplary stent graft 10 shown in FIG. 3 has been removed from the mandrel wherein the stent 20 has radially compressed the stent graft down in diameter to less than the free graft diameter. The stent graft 10 has a free stent graft diameter 16 that is smaller than the free graft diameter. The stent graft is radially compliant meaning it will return to the free graft diameter after expansion to a larger diameter.

Referring now to FIGS. 5 to 8, an exemplary radially compliant stent graft is made by expanding a stent and affixing it over a mandrel having a graft in a free state thereon, attaching the graft to the stent and subsequently removing the stent graft from the mandrel. As shown in FIG. 5, an exemplary graft 40 is configured over a mandrel 70 having a diameter 74 that is substantially the same as the free graft diameter 46. As shown in FIG. 6. an exemplary stent 20 has a free stent diameter 26 that is less than the free graft diameter 46. As shown in FIG. 7, the stent shown in FIG. 6 is expanded radially to an expanded diameter 28 and configured over the graft 40 and mandrel 70 shown in FIG. 5. A bondable tape 62 is shown being wrapped around the stent and graft to adhere the stent and graft together in FIG. 7 to form attachments. The bondable tape may comprise an adhesive or it may comprise a thermoplastic that bonds the stent and graft together when heated. As shown in FIG. 8, the exemplary stent graft 10 shown in FIG. 7 is removed from the mandrel and is radially reduced in diameter to a free stent graft diameter 16. The free stent graft diameter 16 is less than the free graft diameter. The graft has been reduced in diameter to a constricted graft diameter 47. The free stent graft diameter may be substantially the same as the free stent diameter 26. The wall 56 of the stent graft is shown in FIG. 8.

As shown in FIG. 9 and FIG. 10, the exemplary stent graft 10 shown in FIG. 8, is configured in an aneurysmal sack 90 of a vessel 80. As shown in FIG. 9 the stent graft is expanded radially as indicated by the bold arrows, due to the existence of a pressure gradient across the wall of the stent graft. in this example, blood flow to the aneurysmal sack has been excluded and therefore the pressure within the stent graft Pd is greater than the pressure within the aneurysmal sack Pv resulting in the radially compliant stent graft 10 expanding within the aneurysmal sack to an expanded diameter 82, The stent is radially compliant and the graft has stored circumferential length to enable it to expand in diameter. As shown in FIG. 10, the stent graft has a smaller diameter 84 from that shown in FIG. 9, due to non-exclusion of blood flow to the aneurysmal sack and therefore not creating a pressure gradient across the wall of the stent graft. In this example, the pressure, within the stent graft Pd may be substantially the same as the pressure within the aneurysmal sack Pv. The changes in the diameter of the stent graft would follow pressure changes due to systolic and diastolic blood pressure changes. As a result of non-exclusion of the blood flow to the aneurysm, the stent graft may have a diameter that is substantially the free stent graft diameter since there is no pressure differential across the wall.

As shown in FIG. 11A, an exemplary stent graft 10 has attachment points 66, 66' between the graft and the stent. The attachment points or attachments 64, 64' may be formed from an adhesive 60 and/or a stitch 67. The graft has stored circumferential lengths of graft material 50, around the perimeter or circumference and between the attachments points 66. The stored radial length 51 enables the graft to expand radially from constricted diameter to an expanded diameter. The stored circumferential length of material may be configured as a fold or pleat 54 between attachment points and may extend along the length of the stent graft. Attachments between the stent and graft may be discrete points or may be linear attachments extending along the length of the stent graft having folded or pleated graft material therebetween the linear attachments.

As shown in FIG. 11B, the exemplary stent graft 10 shown in FIG. 11A has been expanded radially end the stored circumferential length of the graft material 50 has been elongated to enable the stent graft to expand. The graft has a stored circumferential length of material 50 between the attachments 64. As this stored circumferential length is completely extended and the graft approaches the free graft diameter, the force to expand will greatly increase.

As shown in FIG. 12, an exemplary radially compliant stent graft may have a pressure versus diameter profile that is gradual, and linear, as the stent and graft expand together and the stored circumferential length of graft material allows the graft to expand. However, as the stored circumferential length of graft material is fully extended and the graft approaches the free graft diameter, the force may rapidly increase up to the break force of the graft. The graft may be non-elastic and therefore have limited radial expansion above the free graft diameter. An exemplary radially compliant stent graft may be used to indicated a pressure differential across the wall and therefore indicate if blood flow to an aneurysmal sack has been excluded. An exemplary stent graft may have a known diameter versus pressure profiles, as shown in FIG. 12, and through well-known imaging techniques, the pressure differential across the wall of an implanted stent graft may be determined by comparison to the pressure profile. There is a linear region of the pressure very diameter graph and a line may be fit to this linear portion of the graph for determining pressure gradients across the stent graft in vivo. When an exemplary stent graft is implanted across an aneurysmal sack and successfully excludes blood flow to the sack, the change in diameter of the stent graft within the aneurysmal sack, as indicated in FIG. 12, may correlate with the patient's blood pressure profile. When the aneurysmal sack is not successfully excluded the diameter of the stent graft within the span of the aneurysmal sack will have a free stent graft diameter since there will be no pressure differential across the wall.

Referring now to FIGS. 13 to 17, an exemplary radially compliant stent graft is made by expanding a stent over a mandrel 70 and subsequently affixing a graft over the stent in the expanded state. As shown in FIG. 13, an exemplary stent 20 is expanded to an expanded diameter 28 and configured over a mandrel. As shown in FIG. 14, a graft 40 is configured over the stent 20 and mandrel 40. The outer diameter of the stent configured on the mandrel may be substantially the same as the free diameter of the graft 46. The stent and graft may be attached to each other by stitching or applying an adhesive on a portion of the outer surface of the stent, and then removed from the mandrel to produce a radially compliant stent graft 10, as shown in FIG. 15. The radially compliant stent graft 10, shown in FIG. 15 has a free stent graft diameter 16 that is less than the diameter of the mandrel. As shown in FIG. 16, the stent graft 10 is expanded to an expanded diameter 18 by an internal pressure within the conduit formed by the stent graft. As shown in FIG. 17, the graft, being radially compliant, will produce a recovery force, or radial force to return the stent graft 10 back to the free stent graft diameter when the pressure within the conduit is reduced.

As shown in FIG. 18, an exemplary stent graft 10, is configured on a mandrel that is substantially the free graft diameter and is being wrapped with a tape, such as a bondable tape 62 that may bond the stent to the graft. The bondable tape may form the attachments 64 between the stent and the graft. The stent is configured over the graft which is configured on the mandrel having a diameter 74 that is about the free graft diameter. The bondable tape may comprise an adhesive, such as a thermoplastic adhesive that can be melted to bond the stent to the graft. The graft and/or the stent may be coated with an adhesive to enable bonding and attachment of the stent to the graft.

As shown in FIG. 19, the exemplary stent graft shown in FIG. 18 is removed from the mandrel and is constricted down to a free stent graft diameter 16 that is less than the mandrel diameter 74, Referring now to FIGS. 20 to 24, an exemplary radially compliant t graft 10 is made by constricting a graft 40 on a vacuum mandrel 72 and subsequently affixing a stent 20 over the graft in the constricted state. As shown in FIG. 20, an exemplary vacuum mandrel 72 is drawing air from the outer diameter of the mandrel into the interior conduit of the mandrel. The vacuum mandrel may be porous metal or comprise a plurality of holes from the outside surface to the interior conduit. As shown in FIG. 21, the graft 40 shown in FIG. 20 is drawn down radially onto the vacuum mandrel from the free graft diameter 46, shown in FIG. 20, to a constricted diameter 47, and has stored length, such as pleats or folds. As shown in FIG. 22, a stent 20 is configured over the graft shown in FIG. 21. The stent 20 may have a free stent diameter 26. As shown in FIG. 22, the stent 20 and graft 40 are configured on the vacuum mandrel 72. As shown in FIG. 23, the stent is attached to the graft by stitches 67 that form attachments 64. As shown in FIG. 24, the radially compliant, stent graft 10 has been removed from the mandrel 72 of FIG. 23 and has an inner diameter 11 and outer diameter 17.

Referring now to FIGS, 25 to 27, an exemplary radially compliant stent graft 10 is made by constricting a graft 40 over a stent 20 configured on a vacuum mandrel 72. As shown in FIG. 25, an exemplary vacuum mandrel 72 has a stent 20 and a graft 40 configured thereover. An adhesive 60 is configured between the stent and the graft and may be attached to the stent, as shown. The mandrel may have an outer diameter that is substantially the same as the free stent diameter. The graft has a free graft diameter 46 that is larger than the outer diameter of the mandrel. The graft is constricted down onto the stent by the vacuum mandrel, as indicted by the large radially inward pointing arrows in FIG. 26. It is understood that the graft may have to have the end closed to allow the vacuum to draw down the graft. As shown in FIG. 26, the graft is drawn down to a constricted diameter 47 and may be attached to the stent. The stent may comprise adhesive that bonds the graft to the extensions and/or nodes of the stent. As shown in FIG. 27, the radially compliant stent graft 10 has been removed from the mandrel 72 of FIG. 26.

As shown in FIG. 28, an exemplary radially compliant stent graft 10 is disposed across an aneurysmal sack 90 of an artery 91. The stent graft extends from a first end 96 to a second end 98 and extends across the length 93 of the aneurysmal sack. The diameter of the stent graft 92 within the aneurysmal sack 90 is enlarged from the free stent graft diameter. The diameter 94 of the stent graft proximal the ends is smaller than the free stent graft diameter and is approximately the diameter of the healthy artery. The increase in diameter of the radially compliant stent graft within the aneurysmal sack beyond the free stent graft diameter indicates that the stent graft has excluded blood flow to the aneurysmal sack. Therefore, the pressure within the aneurysmal sack, Pa, is less than the pressure within the artery and within the radially compliant stent graft, Pi. This pressure differential across the stent graft wall causes the radial expansion in diameter within the aneurysmal sack.

As shown in FIG. 29, the exemplary radially compliant stent graft 10 is not enlarged in diameter within the aneurysmal sack 90 above the free stent graft diameter, thereby indicating that the blood flow has not been excluded to the aneurysmal sack. The pressure within the aneurysmal sack, Pa, will be approximately the same as the pressure within the stent graft 10 and therefore there will be no substantial change in pressure across the wall of the stent graft. The portion of the stent graft 10 that is within the aneurysmal sack resembles the elastic vasculature of a healthy young individual and undergoes the diameter changes in response to systolic and diastolic arterial pressures. The diameter of the stent graft 92 in the aneurysmal sack is approximately the same as the diameter of the healthy vasculature 91 or the diameter of the end of the stent graft within the healthy vasculature.

As shown in FIG. 30, an exemplary radially compliant stent graft 10 has a pressure indicating section 99. A radially compliant stent graft may be made with a portion, between the ends 96, 98 that is not restrained in diameter by a bondable tape 62. A bondable tape may be wrapped around a radially compliant stent graft when the stent graft is at a free stent graft diameter and the bondable tape may prevent the wrapped portions from expanding radially. The pressure indicating section may be free of bondable tape or other radially limiting attachment and therefore may be free to expand radially as shown in FIG. 31. As shown in FIG. 31 the exemplary radially compliant stent graft 10 of FIG. 30 is disposed across an aneurysmal sack 90 of an artery 91. The pressure indicating section 99 has a length 101 and a diameter 103. The diameter of the pressure indicating section is greater than the diameter of radially constrained portions 106, of the stent graft, thereby indicating that the aneurysm has been excluded and that the pressure within the aneurysmal sack Pa is less than the pressure within the stent graft Pi, as shown in FIG. 30.

As shown in FIG. 32, an exemplary radially compliant stent graft 10 configured in a constriction tube 120. The stent 20 is configured within the graft 40 and this concentric assembly has been pulled into the tube. The tube may be heated to bond a graft and the stent. A stent may comprise a thermoplastic adhesive that melts and creates attachments between the stent and the graft.

Definitions

Radial compliant, as used herein with reference to a stent graft, is defined as a stent graft that will automatically return to a free stent graft diameter when external forces are removed, from both a compressed state of at least 5% reduction from the free stent graft diameter and from a radially expanded state of at least 5% greater in diameter. Preferable the stent graft is radially compliant in expansion from the free stent graft diameter up to 3 to 30% increase in diameter from the free stent graft diameter, including 3% or more, 5% or more, 10% or more, 15% or more, 20% or more, or 30% or more. As described herein, an exemplary stent graft will automatically return to a free stent graft diameter after expansion or compression and can readily expand and contract from a free stent graft diameter.

Attachments, as used herein, are attachments between the stent and the graft and may comprise a bondable tape that is wrapped around the stent graft or configured between the stent and graft, an adhesive material configured between the stent and the graft, such as an adhesive coating on a portion of the stent and the graft, or a stitch. An adhesive may be any suitable type of adhesive including a thermoplastic adhesive that melts to affix the stent to the graft.

Substantially the free graft diameter, as used herein, is at least 80% of the free graft diameter and preferably at least 90% of the free graft diameter, wherein the free graft diameter is the diameter of the graft with no external forces applied.

Constricted graft, as used herein, is a graft that is reduced in diameter from the free graft diameter.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A radially compliant pressure indicating stent graft comprising:
   a) a cylindrical wall;
   b) free stent graft diameter;
   c) an cylindrically shaped elastic stent that is radially compliant in compression and expansion, and having:
      i) a free stent diameter; and
      ii) a proximal end;
      iii) a distal end;
      iv) a middle portion; and
      v) a length from the proximal end to the distal end;
   d) a radially oversized non-compliant cylindrically shaped graft having:
      i) a free graft diameter;
      ii) a constricted diameter; and
      iii) a length;
   wherein the free graft diameter is larger than the free stent diameter and wherein the radially compliant pressure indicating stent graft is radially expandable from the free stent diameter to the free graft diameter and is elastic between the free graft diameter and the free stent diameter;
   wherein the free graft diameter is at least 5% greater than the free stent diameter;
   e) attachments between the stent and the graft that affix the stent to the graft;
   wherein the free stent graft diameter is substantially the same as the free stent diameter and wherein there is a stored radial length of the graft between said attachment points;
   wherein the stent graft is radially expandable to an expanded stent graft diameter that is substantially the same as the free graft diameter and radially compliant between the expanded stent graft diameter and the free stent graft diameter;
   wherein the attachments comprise a bondable tape, and wherein the bondable tape is non-compliant and is wrapped over an outer surface of the stent graft.

2. The radially compliant stent graft of claim 1, wherein the elastic stent is Nitinol.

3. The radially compliant stent graft of claim 1, wherein the graft consists essentially of polymer.

4. The radially compliant stent graft of claim 1, wherein the stent graft length remains substantially the same between the free stent graft diameter and the expanded stent graft diameter.

5. The radially compliant stent graft of claim 1, wherein the graft comprises expanded polytetrafluoroethylene.

6. The radially compliant stent graft of claim 1, wherein the free graft diameter is at least 10% greater than the free stent diameter.

7. The radially compliant stent graft of claim 1, wherein the stent is configured over the graft.

8. The radially compliant stent graft of claim 1, wherein the stent is configured within the graft.

9. The radially compliant stent graft of claim 1, having a linear diameter pressure differential profile, whereby an expanded diameter of the stent graft correlates to a pressure differential across the wall of the stent graft.

10. A method of making a radially compliant stent graft comprising the steps of:
    a) providing a cylindrically shaped elastic stent having:
       i) a free stent diameter; and
       ii) a length;
       wherein the elastic stent is compliant in compression and expansion;
    b) providing a radially oversized cylindrically shaped graft having:
       i) a free graft diameter that is at least 5% larger than the free stent diameter;
       ii) a constricted diameter; and
       iii) a length;
       wherein the free graft diameter is greater than the constricted diameter; and
       wherein the elastic stent is radially expandable to at least the free graft diameter and elastic between the free graft diameter and the free stent diameter;
    c) expanding the stent from the free stent diameter to an expanded diameter;
    d) attaching the expanded stent to the graft to form attachments between the stent and the graft that affix the stent to the graft;
       wherein the step of attaching comprises wrapping a bondable tape over an outer surface of the stent graft while configured in an expanded state
    e) allowing the expanded stent to constrict to substantially the free stent diameter thereby creating a stored radial length of the graft between said attachments;
       wherein the stent graft has a free stent graft diameter that is substantially the same as the free stent diameter;
       wherein the stent graft is radially expandable to an expanded stent graft diameter that is substantially the same as the free graft diameter and radially compliant between the expanded stent graft diameter and the free stent graft diameter.

11. The method of claim 10, wherein the step of expanding the stent further comprises the steps of:
    configuring the graft over a mandrel, and
    configuring the stent over the graft that is configured on the mandrel.

12. The method of claim 10, wherein the step of attaching comprises heating the stent graft to bond an adhesive between the stent and the graft.

13. The method of claim 10, wherein the step of attaching comprises stitching the stent to the graft.

14. The method of claim 10, wherein the step of expanding the stent further comprises the steps of:
    configuring the stent over a mandrel that is larger in diameter than the free stent diameter, and subsequently configuring the graft over the stent that is configured on the mandrel.

* * * * *